United States Patent [19]
Goldsmith

[11] Patent Number: 4,580,901
[45] Date of Patent: Apr. 8, 1986

[54] FLUID SAMPLE CELL
[75] Inventor: Herbert Goldsmith, Rockville, Md.
[73] Assignee: Pacific Scientific Company, Anaheim, Calif.
[21] Appl. No.: 547,240
[22] Filed: Oct. 31, 1983
[51] Int. Cl.[4] .......................................... G01N 21/01
[52] U.S. Cl. .................... 356/409; 356/246; 356/243; 250/576
[58] Field of Search ............... 356/409, 410, 411, 244, 356/246, 440, 36; 350/533; 250/352, 443.1, 576

[56] References Cited
U.S. PATENT DOCUMENTS

| 1,848,874 | 3/1932 | Fitz Gerald. | |
|---|---|---|---|
| 2,649,011 | 8/1953 | Black | 88/14 |
| 2,707,900 | 5/1955 | Maresh et al. | 88/14 |
| 3,141,094 | 7/1964 | Strickler | 250/218 |
| 3,164,663 | 1/1965 | Gale | 88/14 |
| 3,501,242 | 3/1970 | deMey, II et al. | 356/246 |
| 3,524,066 | 8/1970 | Blakkan | 250/218 |
| 3,552,864 | 1/1971 | Shields | 356/246 |
| 3,628,872 | 12/1971 | Miranda | 356/201 |
| 3,644,045 | 2/1972 | Walsh | 356/314 |
| 3,646,313 | 2/1972 | Gorgone et al. | 356/246 |
| 3,704,951 | 12/1972 | Chupp | 356/75 |
| 3,740,155 | 6/1973 | Keller et al. | 356/180 |
| 3,773,424 | 11/1973 | Selgin | 356/181 |
| 3,822,947 | 7/1974 | Aday, Jr. | 356/246 |
| 3,861,788 | 1/1975 | Webster | 356/418 |
| 3,869,215 | 3/1975 | Nolan | 250/576 |
| 3,886,364 | 5/1975 | Walker et al. | 250/343 |
| 4,021,124 | 5/1977 | Sarstedt | 250/576 |
| 4,192,614 | 3/1980 | De Mey, II et al. | 356/410 |
| 4,278,887 | 7/1981 | Lipshutz et al. | 250/432 |
| 4,405,235 | 9/1983 | Rossiter | 356/440 |

FOREIGN PATENT DOCUMENTS
0072849  6/1980  Japan .................... 356/246

Primary Examiner—F. L. Evans
Assistant Examiner—Joel L. Harringa
Attorney, Agent, or Firm—Lane and Aitken

[57] ABSTRACT

A fluid sample cell for the spectroscopic analysis of a sample includes a fluid-tight sample compartment defined by a radiant energy transmissive top, a side wall, and a bottom having a reflective surface. The bottom is heat conductive and comprises an external surface which defines a hollow well adapted to receive a hot plate. A fluid sample cell is also provided wherein a side wall of a sample compartment defines an entry port and an exit port such that, when the cell is in a substantially vertical position, one of the ports is located above and one below the compartment. A fluid sample cell is also provided wherein a side wall of the sample compartment is provided with a pocket for collecting impurities when the cell is in a substantially vertical position, wherein the pocket is disposed above and/or below the sample compartment. The sample cell can be pivotally connected to a support, whereby a sample can be introduced or purged while the cell is in a vertical position and the sample can be irradiated and a hot plate inserted into the cell when the cell is in a horizontal position. A method for introducing a sample to such a cell is also disclosed.

30 Claims, 5 Drawing Figures

FLUID SAMPLE CELL

BACKGROUND OF THE INVENTION

1. Field of the Invention

This invention relates to an improved fluid sample cell for the spectroscopic analysis of a fluid sample.

2. Description of the Prior Art

A number of fluid sample cells are known in the art for the containment of fluid samples during transmission spectroscopic analysis. The cells typically include one opening for the entrance and one opening for the exit of radiant energy, and are positioned in a spectroscopic instrument where a contained sample is irradiated with radiant energy. After passing through the sample, the radiant energy is detected and analyzed to determine the absorptive characteristics of the sample or a constituent thereof. The sample cell described herein represents an improvement over previously known sample cells of this type.

Many types of samples that undergo spectroscopic analysis must be maintained at narrowly defined, elevated temperatures during the analysis. If the temperature is not maintained within a narrow range, the analysis can be rendered inacurate by virtue of unwanted variations in the absorption characteristics of the sample. In the prior art, various means have been provided to effect the heating of spectroscopic samples, but the heating and maintenance of samples in appropriate temperature ranges has been deficient in the prior art devices in terms of accuracy, convenience and efficiency.

A fluid sample cell should also be provided with some means for samples to be introduced and removed. The introduction and removal of samples can be done batch-wise, wherein one sample is introduced and removed before another is introduced, or the introduction and removal can be effected in a continuous manner, whereby a first sample may be purged by the simultaneous introduction of a subsequent sample. Because spectroscopic instruments typically irradiate sample cells when the cell is in a horizontal position, and because samples are often introduced and/or removed from the cell while in this horizontal position, the sample cells of the prior art typically are provided with inlet and outlet ports that are disposed laterally of the sample compartment and which are intended to carry the sample when the cell is in the horizontal position. It has now been found that this lateral filling arrangement is deficient because it fails to efficiently introduce and purge samples.

When unwanted impurities are present in a sample that is analyzed, the analysis can be rendered inaccurate. Such impurities are defined broadly herein to include lighter gaseous impurities, such as air, in a liquid sample or heavier liquid impurities, such as water, in a gaseous sample. The term impurities is also intended to include portions of prior samples that are not completely purged when a subsequent sample is introduced. Many prior art systems fail to provide any convenient means for the removal of such impurities.

Thus, it can be seen that the sample cells of the prior art are deficient in a number of respects, and that there is a need in the art for an improved sample cell which corrects the aforementioned deficiencies. To this end, the present invention is directed. Other objectives of the present invention will become apparent from the following discussion.

SUMMARY OF THE INVENTION

In accordance with the present invention, a fluid sample cell for the spectroscopic analysis of a sample is provided which includes a fluid-tight sample compartment defined by a radiant energy transmissive top, a side wall, and a bottom having a reflective surface. The bottom is heat conductive and comprises an external surface which defines a hollow well adapted to receive a hot plate.

In another embodiment of the present invention, a fluid sample cell for the spectroscopic analysis of a sample is provided which includes a fluid-tight sample compartment defined by a top, a side wall, and a bottom, wherein at least one of the top and the bottom define an opening for the entry and exit of radiant energy into and out of the compartment. The side wall defines an entry port and an exit port such that, when the cell is in a substantially vertical position, one of the ports is located above and one below the compartment.

In still another embodiment, the side wall of the fluid sample cell is provided with at least one pocket for collecting impurities when the cell is in a substantially vertical position, the impurities having a different density than the sample. The pocket is disposed above and/or below the sample compartment, depending upon whether the impurities are more or less dense than the sample.

A pivoting arrangement is also provided for the sample cell, whereby a sample can be introduced or purged while the cell is in a vertical position and the sample can be irradiated and a hot pad inserted into the cell when the cell is in a horizontal position.

DESCRIPTION OF THE PREFERRED EMBODIMENTS

The invention will now be described in detail, with reference to the drawings.

Figure 1:
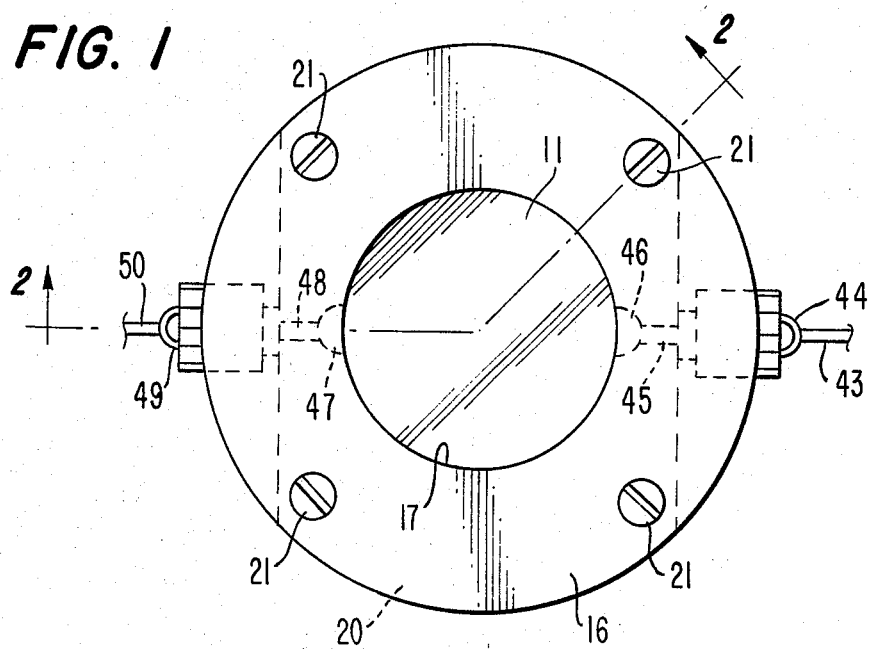
FIG. 1 is a plan view of a fluid sample cell in accordance with the invention.
Figure 2:
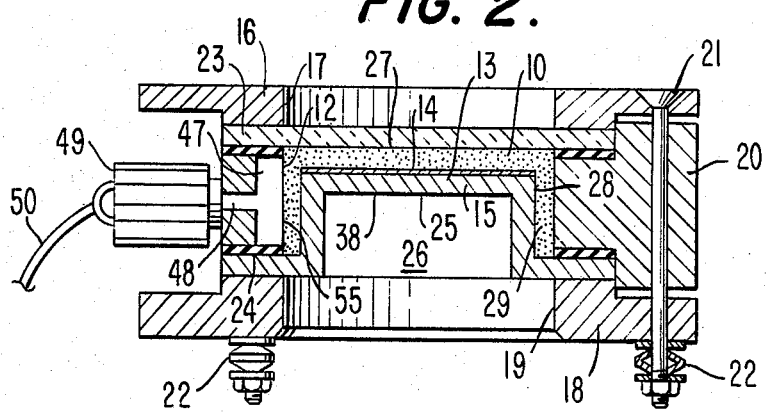
FIG. 2 is a sectional view of the fluid sample cell of FIG. 1, taken along section line 2—2.

As depicted in FIGS. 1 and 2, the fluid sample cell of the present invention can be generally cylindrical in shape, and comprises a fluid-tight compartment 10 for the containment of a fluid sample. The compartment is defined by a radiant energy transmissive top 11, a side wall 12, and a bottom 13. In the embodiment depicted in FIG. 2, the bottom is comprised of a diffused reflective surface 14 and a heat conductive brass base member 15. Transmissive top 11 is held in place by a top retaining member 16 which defines an annular opening 17. Bottom 13 is retained in place by bottom retaining member 18, and bottom retaining member 18 defines annular opening 19. Annular block 20 separates transmissive top 11 and bottom 13 and defines a portion of side wall 12. Bolts 21 secure top and bottom retaining members 16, 18 to annular block 20, and are secured by Belleville washers 22. A top gasket 23 and bottom gasket 24 are provided to maintain the sample compartment fluid-tight.

As best seen in FIG. 2, bottom 13 has an external surface 25 which defines a hollow well 26 that is adapted to receive a heating element. Because bottom 13 is composed of materials that are heat conductive, heat generated in well 26 passes through bottom 13 and into compartment 10, in order to heat a sample 27 contained therein. In the embodiment depicted in FIG. 2, the interior surface 28 of bottom 13 protrudes into sample compartment 10 in order to define an annular channel 29 between side wall 12 and interior surface 28. As a result of this arrangement, a portion of well 26 is disposed within the periphery of annular channel 29. In practice, the distance between bottom 13 and side wall 12 can be about 1 mm., while the distance between bottom 13 and top 11 can be about 1 to 3 mm.

Figure 3:
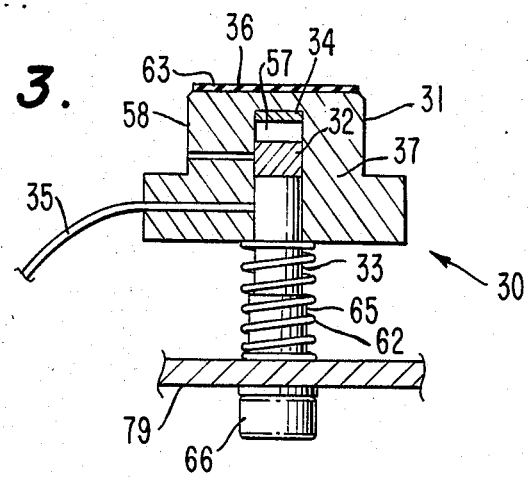
FIG. 3 is a side view of a hot plate used to supply heat to a compartment of the device depicted in FIG. 2.

A heated fluid cell system in accordance with the present invention comprises the fluid sample cell depicted in FIG. 2 and a hot plate 30, as depicted in FIG. 3. The hot plate is designed to fit within well 26 in order to generate heat in the well. Subsequently, the heat is transmitted through bottom 13 into sample compartment 10. The hot plate includes an enclosure 31 which is made of heat conductive material and which contains a heating element 32. The heating element can be disposed on a supporting shaft 33, and the shaft can further support a thermostat. While heat in compartment 10 can be regulated without the use of a thermostat, whereby regulation is achieved by carefully selecting and maintaining a constant temperature for heating element 32, the use of a thermostat is preferred. The thermostat can be provided with a temperature sensing element 34 and a control 57 for activating and deactivating element 32 to maintain a constant temperature. The control 57 can be supported on shaft 33 or can be located remotely from hot plate 30 and connected to the temperature sensing element 34 and heating element 32 by wiring. An electrical supply source can be connected to the heating element and thermostat by cable 35.

A resilient heat conductive pad 63, such as a rubber or elastomeric material filled with heat conducting particles, is mounted on the top of the enclosure 31 in order to transmit heat from the enclosure to surface 36. Pad 63 contacts horizontal portion 38 of the exterior surface of bottom 13 of the sample cell. Hot plate 30 can also be formed such that other surfaces, for example, vertical annular surface 58, contact mating surfaces of bottom 13 when hot plate 30 is inserted into well 26. A biasing means is provided to compress pad 63 against horizontal portion 38 to provide good thermal contact between the surface 38 and the hot plate. Thus, in the embodiment depicted in FIG. 3, supporting shaft 33 is received in a cylindrical guideway 65 and the guideway is attached to the floor 79 of a support. A portion of the shaft extends through a hole in the floor 79 and is provided with a stop lug 66 to keep hot plate 30 from being separated from structure 41 due to the action of a spring 62 which surrounds shaft 33 and guideway 65, such that the hot plate is biased upwardly from the floor.

Figure 4:
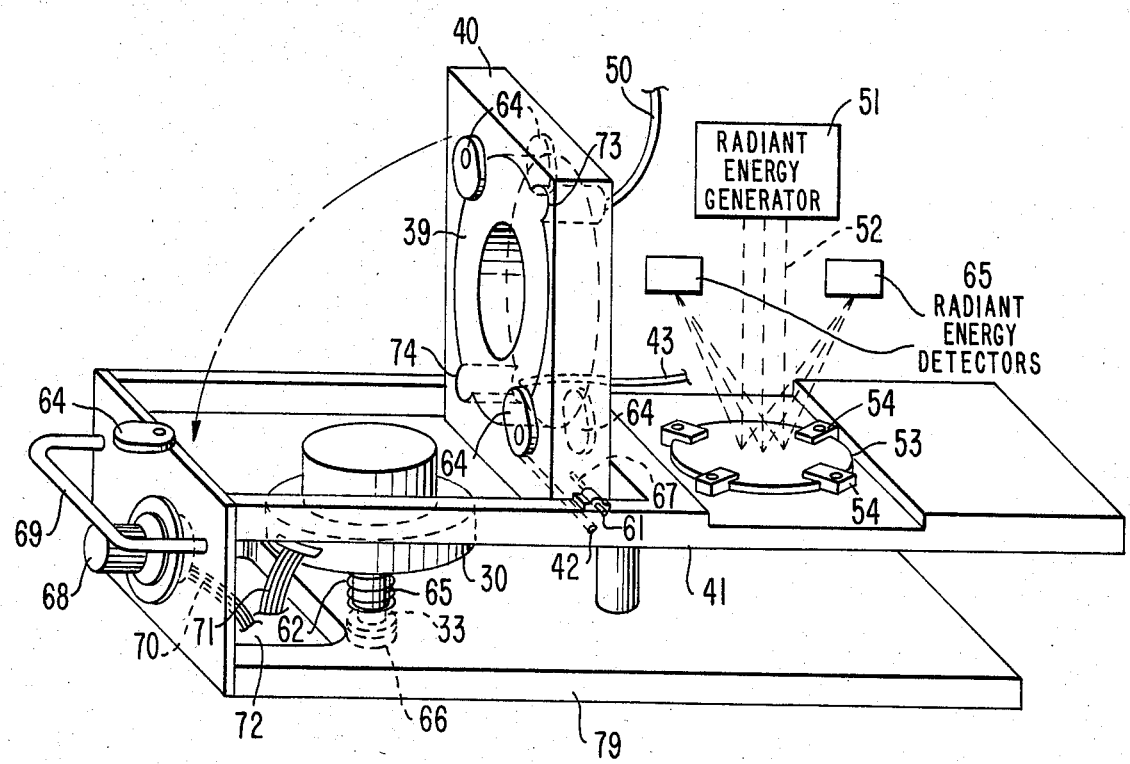
FIG. 4 is a perspective view of a spectroscopic instrument containing the fluid sample cell and hot plate depicted in FIGS. 1, 2 and 3.

Means are provided for pivoting the sample cell from a substantially horizontal position to a substantially vertical position. One means for pivoting the cell is depicted in FIG. 4. There, the fluid sample cell 39 is contained in a retaining block 40 where it is held by conventional means such as clips 64, and the retaining block 40 is connected to a supporting structure 41 by means of an axle 42 which is attached to and supported on both ends by structure 41 and which extends through block 40. The axle can be pivotally mounted in structure 41, or can be fixedly mounted such that block 40 is allowed to pivotally rotate on the axle. Axle 42 need not be continuous, but can instead be in the form of relatively short studs extending inwardly from each side of structure 41. Recesses 73, 74 are provided in block 40 to leave room for the Luer valves and conduits of the sample cell. As indicated by the arcuate arrow in FIG. 4, the pivoting action provided by axle 42 allows retaining block 40 and sample cell 39 to be disposed in a vertical position or a horizontal position. To maintain the cell in a vertical position, it can be held by hand or secured in any conventional fashion, such as by a slidable pin 61 slidably engaged to structure 41 and receivable in a mating channel 67 of block 40. When in the horizontal position, well 26 of sample cell 39 receives at least a portion of hot plate 30, and the cell is retained in place by the upwardly biasing action of spring 62 and the restricting action of clip 64. Preferably, at least surface 36 will make contact with horizontal bottom 38 of well 26. It will be readily apparent to those skilled in the art that, due to the arcuate path traveled by sample cell 39 when it is lifted away from hot plate 30, sufficient clearance between the internal vertical sides of well 26 and the external vertical sides of hot plate 30 is necessary. As depicted in FIG. 4, a temperature control knob 68 and handle 69 are provided, and connecting wires 70 from the knob and 71 from the hot plate can extend through hole 72 to connect with a power supply and other electronic circuitry.

The present device also comprises means for introducing and purging samples from the fluid sample cell. As depicted in FIG. 1, a sample can be introduced through flexible entry conduit 43 to entry Luer valve 44, and then through entry port 45. Preferably, entry port 45 will comprise a pocket 46, and the entering sample will pass through pocket 46 on the way to sample compartment 10. In exiting sample compartment 10, the sample passes through pocket 47, exit port 48, exit Luer valve 49, and flexible exit conduit 50. As can be seen from FIGS. 1 and 2, entry port 45 and exit port 48, as well as pockets 46, 47 are defined by annular block 20. Pockets 46, 47 are trough-shaped and extend longitudinally along substantially the entire vertical length of channel 29.

As best depicted in FIG. 4, fluid sample cell 39 can be pivoted to a vertical position, whereby entry conduit 43 is disposed below sample compartment 10, and exit conduit 50 is disposed above compartment 10. When fluid cell 39 is disposed in this vertical position, the introduction and/or purging of a sample or samples is preferably undertaken. The introducing and purging of samples can be effected in a continuous or batch-wise fashion. Thus, a sample can be introduced and purged before the introduction of a subsequent sample, or a first sample can be purged simultaneously with introduction of a subsequent sample. It has been found that the introduction and purging of samples when the sample cell 39 is in a vertical position is much more efficient and effective than when the cell is in a horizontal position. It would also be within the scope of the invention to reverse the positions of the entry and exit means, whereby the entry means would be disposed above and the exit means above the compartment.

In the embodiment depicted in FIG. 4, the sample cell 39 is disposed in a pivoting fashion, as described above.

This represents an especially preferred embodiment, since spectrographic apparatus commercially available are often arranged to irradiate fluid samples which are in a horizontal position, whereby the radiant energy of a radiant energy generator is directed in a vertically downward fashion. Thus, as depicted in FIG. 4, sample cell 39 can be provided with a new sample when the sample cell is in a vertical position and, when irradiation of the sample is to be undertaken, sample cell 39 is pivoted to a horizontal position, as indicated by the arcuate arrow, so that compartment 10 is positionable in the path of radiant energy from a radiant energy generator. The direction of radiant energy emitted from a radiant energy generator 51 of a spectroscopic apparatus is indicated by the parallel arrows 52 in FIG. 4. In this embodiment, the sample cell, after being pivoted to a horizontal position, can be positioned for irradiation by sliding support 41 horizontally rearward so that sample cell 39 is positioned beneath radiant energy generator 51. It is also within the scope of this invention that an apparatus be used wherein the radiation generating means is disposed laterally of the sample compartment, whereby irradiation is effected when the sample cell is in a vertical position and the need for disposing the cell horizontally is eliminated.

As further depicted in FIG. 4, the hereinabove described means for introducing and purging a fluid sample and the hereinabove described heated fluid cell system are included in the same device. However, for samples which need no heating means, hot plate 30 can be done away with and, if desired, bottom 13 can be made radiant energy transmissive, whereby radiant energy would be passed through both the radiant energy transmissive top and radiant energy transmissive bottom to be detected by radiant energy detectors disposed below the bottom.

It is important to calibrate a spectroscopic instrument by determining absorptive characteristics of a standard before measuring the absorptive characteristics of the unknown. The device depicted in FIG. 4 comprises a convenient means for calibrating the instrument. Thus, support frame 41 is slidable in a horizontal direction and supports a ceramic disc 53 which is retained by latches 54. The sliding action of support 41 enables either the compartment of fluid cell 39 or the standard 53 to be positioned in the path of the radiant energy generated by radiant energy generator 51.

Figure 5:
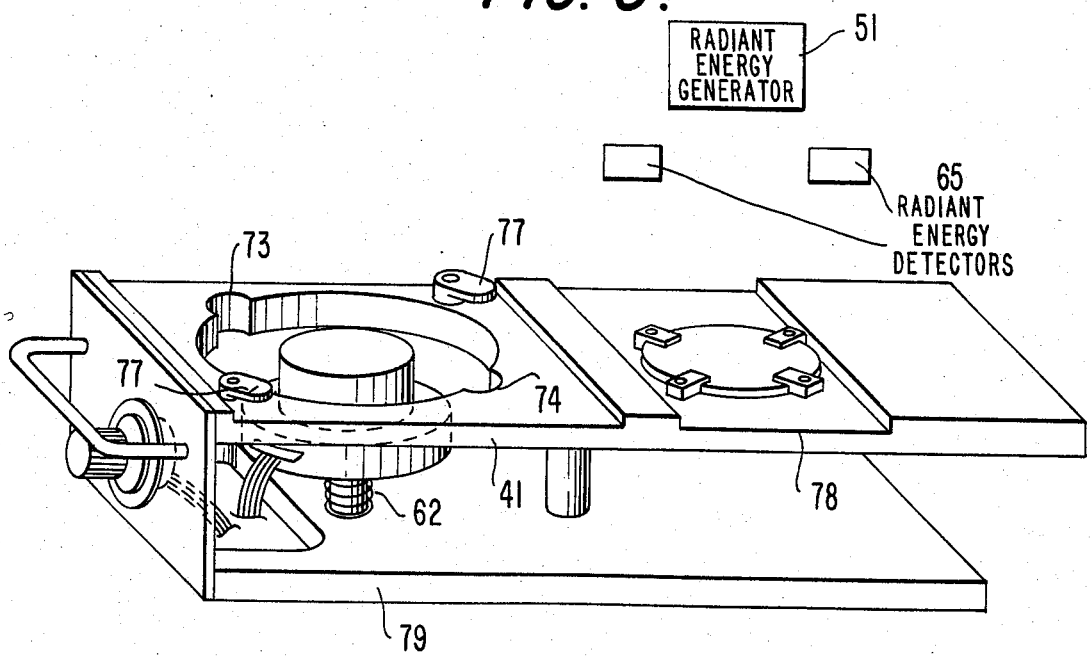
FIG. 5 is a perspective view of a spectroscopic instrument intended for receiving the fluid sample cell depicted in FIGS. 1 and 2.

In an alternative embodiment, depicted in FIG. 5, the fluid sample cell is received directly in a top surface of structure 41, and retained in place by the upwardly biasing action of spring 62 and recessed latches 77. The fluid cell can be filled in a vertical position before being placed in the structure 41. Structure 41 is caused to slide along a mating channel which is affixed to a base of the spectroscopic instrument. If sliding is effected in this fashion, latches 77 are recessed and recess 78 is preferably provided so that structure 41 can slide freely.

As mentioned above, a sample to be tested in spectroscopic analysis can contain unwanted impurities which may adversely affect the accuracy of the measurements of the spectroscopy instrument. The present invention provides a means for collecting air or other impurities that have a density different from the sample. The means consists of at least one pocket 46, 47 which is defined by side wall 12 of annular block 20, as depicted in FIG. 2. Preferably, two pockets will be provided, and they will constitute portions of respective entry port 45 and exit port 48. The pockets are troughshaped and extend substantially the entire vertical length of channel 29.

Pockets 46, 47 operate to collect air and other impurities when sample cell 39 is disposed in a substantially vertical position, as depicted in FIG. 4. In this position, impurities having a density less than the sample will be received in pocket 47, which will be disposed above sample compartment 10, and impurities having a density greater than the sample will be received in pocket 46, which will be disposed below the sample. When the sample is being purged through an exit port which is adjacent to pocket 46 or 47, the impurity that has been collected in the pocket will be purged as well.

In a specific embodiment, annular block 20 can be composed of stainless steel in order to prevent the corrosive effect of certain samples which may be tested in the sample cell. Top retaining member 16 and bottom retaining member 18 can be composed of anodized aluminum. Top and bottom gaskets 23, 24 can be Kal-Rez gaskets, which are manufactured by DuPont. The Belleville washers which may be used in this device allow pressure on gaskets 23, 24 to remain the same, despite possible fluctuations in length of bolts 21.

Having thus described the invention in a number of specific embodiments, it will be readily apparent to those skilled in the art that numerous modifications can be made that are within the inventive scope of the present teachings.

I claim:

1. A heated fluid sample cell system for the spectroscopic analysis of a sample comprising a sample cell including a fluid-tight sample compartment defined by a radiant energy transmissive top, a side wall, and a bottom having a reflective surface adjacent said compartment, wherein said bottom is heat conductive and comprises an external surface which defines a hollow well adapted to receive a hot plate positioned on an axis passing centrally through said compartment, means to heat the fluid in said compartment comprising a hot plate shaped to be received in or removed from said well primarily by relative movement between said hot plate and sample cell along said axis.

2. The fluid sample cell according to claim 1, wherein an interior surface of said bottom which is adjacent to said compartment protrudes into said compartment to define a channel between said wall and a portion of said interior surface.

3. The fluid sample cell according to claim 2, wherein at least a portion of said well is disposed within said channel.

4. The fluid sample cell according to claim 1, wherein said compartment is further defined by a top gasket disposed between said top and said side wall and a bottom gasket disposed between said side wall and said bottom.

5. The fluid sample cell according to claim 1, wherein said bottom comprises a brass base member adjacent to said reflective surface.

6. The fluid sample cell according to claim 1, wherein said reflective surface is a diffuse reflector.

7. A heated fluid sample cell system according to claim 1, wherein said hot plate comprises a heating element positioned to be received in said well when said hot plate is received in said well.

8. The heated fluid cell system according to claim 7, wherein said plate comprises a heated surface which receives heat from said element, said heated surface contacting said bottom when said plate is received in said well.

9. The heated fluid cell system according to claim 7, wherein said plate further comprises a thermostat, which senses the temperature of said hot plate, and controls the operation of said element to maintain a constant temperature.

10. The heated fluid cell system according to claim 1, wherein said plate further comprises a resilient heat conductive pad positioned to contact said bottom in said bottom in said well, said system further comprising means for compressing said pad against said bottom when said plate is received in said well.

11. The heated fluid cell system according to claim 1, further comprising means mounting said cell to provide for insertion and removal of said plate from said well.

12. The heated fluid cell system according to claim 11, further comprising a support which fixedly supports said plate and pivotally supports said cell, whereby said cell can be pivotally disposed in a first position, whereby said plate is inserted in said well, and a second position, whereby said plate is removed from said well.

13. The heated fluid cell system according to claim 12, wherein said first position is a substantially horizontal position and said second position is a substantially vertical position, and wherein said side wall defines an entry port and an exit port, one port being disposed above and one port being disposed below said compartment when said cell is in said vertical position.

14. The heated fluid cell system according to claim 13, wherein at least one of said ports comprises a pocket for collecting impurities which have a different density than said sample.

15. An apparatus for the spectroscopic analysis of a sample comprising
   a fluid sample cell for the spectroscopic analysis of a sample comprising a fluid-tight sample compartment defined by a top, a side wall, and a bottom, at least one of said top and said bottom defining at least one opening for the entry and exit of radiant energy into and out of said compartment, wherein said side wall defines an entry port and an exit port such that, when said cell is in a substantially vertical position, one of said ports is located above and one below said compartment, and
   a support for holding said cell in a substantially vertical position,
   wherein a sample is at least introduced or purged from said compartment when said cell is in said substantially vertical position.

16. The apparatus according to claim 15 further comprising a radiant energy generator disposed above said cell, wherein said cell is pivotally connected to said support such that said cell can be pivoted to said substantially vertical position and a substantially horizontal position whereby, when in said horizontal position, radiant energy generated by said generator passes through said compartment.

17. The apparatus according to claim 15, wherein at least one of said ports comprises a pocket shaped to collect at said one of said ports impurities which have a different density than said sample.

18. The apparatus according to claim 16, further comprising a standard, whereby said support is slidable and comprises said standard, such that the sliding of said sliding support causes either said fluid sample cell or said standard to be disposed below said radiant energy generator.

19. The apparatus according to claim 16, wherein said bottom comprises a reflective surface, is heat conductive, and further comprises an external surface which defines a hollow well adapted to receive a hot plate.

20. The apparatus according to claim 19, further comprising a hot plate fixedly attached to said support, such that said cell receives said hot plate in said well when in said substantially horizontal position.

21. A fluid sample cell for the spectroscopic analysis of a sample comprising a fluid-tight sample compartment defined by a top, a side wall, and a bottom, at least one of said top and said bottom defining at least one opening for the entry and exit of radiant energy into and out of said compartment, wherein said side wall defines at least one pocket for collecting impurities when said cell is in a substantially vertical position, said impurities having a different density than said sample, wherein said pocket is disposed above said sample compartment when said impurities are less dense than said sample and below said sample compartment when said impurities are more dense than said sample and wherein said side wall further defines an entry port and an exit port such that, when said cell is in said substantially vertical position, one of said ports is located above and one below said compartment, said at least one pocket being disposed adjacent to one of said ports, such that impurities collected in said at least one pocket are removed through said one of said ports.

22. The fluid sample cell according to claim 21, wherein said at least one pocket is disposed above said sample and said impurity is less dense than said sample.

23. The fluid sample cell according to claim 22, wherein said impurity is air.

24. An apparatus for the spectroscopic analysis of a sample comprising the sample cell according to claim 21, a radiant energy generator disposed above said sample cell, and a support for said sample cell, wherein said sample cell is pivotally connected to said support, whereby said impurities are collected in said at least one pocket and removed through said one of said ports when said cell is pivoted to said substantially vertical position and wherein radiant energy generated by said generator is transmitted to said sample compartment when said cell is pivoted to a substantially horizontal position.

25. The fluid sample cell according to claim 21 wherein said compartment comprises an annular channel defined by said side wall and an inwardly protruding interior surface of said bottom, wherein said pocket extends along substantially the entire length of said channel.

26. A method for introducing a sample to a fluid sample cell for the spectroscopic analysis of a sample, said cell comprising a fluid-tight sample compartment defined by a top, a side wall, and a bottom, at least one of said top and said bottom defining at least one opening for the entry and exit of radiant energy into and out of said compartment, wherein said side wall defines an entry port and an exit port such that, when said cell is in a substantially vertical position, one of said ports is located above and one below said compartment, the method comprising the steps of
   disposing said cell in said substantially vertical position,
   introducing a new sample through said entry port,
   disposing said cell in a substantially horizontal position, and passing radiant energy through said sample compartment.

27. The method according to claim 26 wherein said entry port is disposed below and said exit port is disposed above said compartment.

28. The method according to claim 27 wherein, prior to introducing said new sample, said compartment contains a prior sample, such that as said new sample is being introduced through said entry port, said prior sample is being purged through said exit port.

29. The method according to claim 26 wherein said cell further comprises at least one pocket adjacent to at least one of said entry port and said exit port such that, while said cell is disposed in said substantially vertical position, the method further comprises the steps of collecting impurities in said at least one pocket and purging said impurities through said exit port.

30. A method of analyzing a fluid sample comprising providing a fluid sample cell including a fluid tight sample compartment defined by a top, a sidewall, and a bottom, said sidewall having ports to said compartment on opposite sides thereof with at least one of said top and bottom defining an opening for the transmission of radiant energy, arranging said compartment vertically with one of said ports directly above the other, introducing a sample to be analyzed into said compartment through one of said ports while purging the fluid already contained in said compartment through the other of said ports while said compartment is arranged vertically, and then irradiating said sample in said compartment while detecting radiant energy emanating from said compartment.

* * * * *